United States Patent [19]

Cousin

[11] Patent Number: 4,874,610
[45] Date of Patent: Oct. 17, 1989

[54] TALL OIL NEUTRALS TO PROTECT PLANTS FROM INSECTS AND THE LIKE

[75] Inventor: Michael J. Cousin, Circleville, Ohio

[73] Assignee: The Mead Corporation, Dayton, Ohio

[21] Appl. No.: 65,434

[22] Filed: Jun. 23, 1987

[51] Int. Cl.⁴ ............................................. A01N 65/00
[52] U.S. Cl. ........................ 424/196.1; 424/DIG. 10; 514/919
[58] Field of Search ................... 424/196.1, DIG. 10; 514/919

[56] References Cited

PUBLICATIONS

"The Effect of a Purified Extract of Fruits of Azadirachta Indica on Leptinotarsa Decemlineata Say (Coleoptera, Chrysomelidae)." L. ang. Ent. 82 (1976) 169-176 R. Steets.

"Effect of Some Pure Fractions of Extracts from Neem (Azadirachta Indica) Seeds on the Feeding Activity and Metamorphosis of Epilachna Varivestis (Col. Coccinellidae)" Z. Angew. Entomologie: vol. 89; 179-188 (1980) . H. Schmutterer and H. Rembold.

*Primary Examiner*—John W. Rollins
*Attorney, Agent, or Firm*—Smith & Schnacke

[57] ABSTRACT

Plants are protected from insects and mites by the application of tall oil neutrals to the plants. The method can prevent insects and mites from eating on the plants, sterilize the insects and mites, or destroy the insects and mites.

8 Claims, No Drawings

TALL OIL NEUTRALS TO PROTECT PLANTS FROM INSECTS AND THE LIKE

BACKGROUND OF THE INVENTION

The present invention relates to a method for protecting plants from insects, mites, and similar plant pests, and more particularly, to a method for protecting plants through the application of tall oil neutrals to the plants.

For years, the paper making industry has been faced with the problem of what to do with the black liquor created during the Kraft pulping of pine. In order to make the pulping process as economical as possible, the industry has strived to seek applications for the various black liquor components and products derived therefrom.

Kraft or tall oil soap is one by-product of black liquor for which commercial uses exist. Tall oil soap is converted to crude tall oil by acidification with sulphuric acid. This conversion, however, creates another waste product, namely, tall oil neutrals.

SUMMARY OF THE INVENTION

The present invention is advantageous because it provides a method for protecting plants from insects, mites, and similar pests which comprises the step of applying tall oil neutrals to plants. It responds to the paper making industry's need to establish commercially viable applications for black liquor components.

The exact composition of tall oil neutrals will vary with their source and method of isolation. As a general rule, however, they are characterized in that they are the tall oil soap fraction which is insoluble in acid or basic solutions. Commercially, tall oil neutrals are isolated from tall oil soap by extraction of tall oil soap with an organic solvent such as a mixture of acetone and methanol. The tall oil neutrals comprise diterpene alcohols, diterpene, aldehydes, fatty alcohols, sterols, and triterpene alcohols. The insecticidally active component of the tall oil neutrals is believed to be diterpene alcohols and/or diterpene aldehydes.

Canadian crude tall oil is a preferred source of neutrals for the present method because Canadian crude contains a higher percentage of neutrals than other sources. Typically, Canadian crude tall oil contains 17-40 percent rosin acids, 33-44 percent fatty acids, 13-32 percent neutrals, and 13-19 percent unknown acids. In contrast, southern tall oil contains only about 5 percent neutrals.

Thus, an object of the present invention is to provide a useful application for tall oil neutrals.

An additional object of the present invention is to provide a method for protecting plants from insects.

In one embodiment, the present invention provides a method for protecting plants from insects, mites, and similar pests which comprises the step of applying tall oil neutrals to the plants.

Other objects and advantages of the present invention will be apparent from the following description and the appended claims.

DETAILED DESCRIPTION OF THE INVENTION

The method of the present invention for protecting plants from insects, mites, and similar pests comprises the step of applying tall oil neutrals to plants. The plants are believed to be protected by one or more of the following actions: by preventing feeding on the plants, by preventing reproduction, and/or by killing the insects, their larve, or eggs.

The method of the present invention is useful against various insects and mites including cabbage loopers such as *Trichoplosia ni*, aphids, spidermites such as *Tetranychus urticae* etc. The method is useful in protecting numerous growing plants including woody plants such as ficus, schefflera and jade. The formulations used in the present invention appear to be toxic to foliage plants such as beans and chrysanthemums.

Typically, the tall oil neutrals are applied to the plants in diluted form, and more particularly, as a solution or an oil-in-water dispersion. The solution or dispersion may contain about 5 to 40 percent by weight tall oil neutrals. To form a solution, the tall oil neutrals may be dissolved in a non-phytotoxic solvent such as kerosene. Other plant-safe solvents may also be used such as benzene, toluene, xylene, kerosene, diesel fuel, fuel oil, petroleum naphtha, acetone, methyl ethyl ketone, cyclohexanone, carbon tetrachloride, chloroform, trichloroethylene, perchloroethylene, ethyl acetate, amyl acetate, butyl acetate, ethylene glycol monomethyl ether, diethylene glycol monomethyl ether, methanol, ethanol, isopropanol, amyl alcohol, isopropyl alcohol, ethylene glycol, propylene glycol, butyl carbitol acetate, and glycerine. A preferred solvent is isopropyl alcohol and water.

To form a dispersion in accordance with the present invention, the tall oil neutrals may be dispersed directly or pre-dissolved in one of the above solutions. A dispersant or surfactant is typically used. Any conventionally used dispersant can be used in the present invention. The dispersant can be anionic, cationic, or nonionic in character. A preferred surfactant is potassium oleate.

A typical dispersion comprises tall oil neutrals, water, and surfactant. Typically, the surfactant is dissolved in the water and a solution of the tall oil neutrals in a solvent is then added. The amount of tall oil neutrals present in the dispersion can range from about 5 to 40% by weight. The surfactant is present in an amount of up to about 6% by weight of the dispersion.

The solution or dispersion can be one which is used directly or one which is further diluted in a sprayer prior to application. It is also possible to add the tall oil neutrals to a horticultural spray oil such as available from Sun Petroleum Products Company. The amount of tall oil neutrals present in the horticultural spray oil may range from about 5 to 40% by weight. Other conventional additives can be added to the solutions or dispersions.

While the neutrals will typically be applied as a solution or dispersion, the present invention also embraces the use of the tall oil neutrals with an inert solid carrier such as talc, silica, clay, etc.; or as aerosols by dispersing them in air by means of a compressed gas.

The solution or dispersion of the tall oil neutrals may be applied to plant leaves, stems, roots, or surrounding soil which may be accessible to insects and mites. The solution or dispersion can be applied to the plants in a variety of ways. The preferred application technique is spraying the dispersion or solution onto the plants. The plant roots can also be dipped into the solution or dispersion. When spraying, it is usually sufficient to apply the solution or dispersion to plants at about 1 to 3 pounds per acre. The application rate will vary with the type of plant and the means of application. When applying to individual plants larger quantities may be used providing they are not phytotoxic.

The effectiveness of the method varies depending upon numerous factors including insect type, plant type, and plant location. Typically, application of the solution or dispersion may be repeated as needed. Factors such as an outdoor versus an indoor plant control the frequency of application.

The present invention is illustrated in more detail by the following non-limiting Examples:

EXAMPLE 1

The twelve test formulations as shown in Table 1 were evaluated for their effects on second-instar cabbage looper, *Trichoplusia ni*, larva on chrysanthemum leaf discs. T. O. stands for tall oil, IPA stands for isopropyl alcohol, and K-oleate stands for potassium oleate.

TABLE 1

FORMULATIONS EVALUATED

| Formulation Number | Composition | % T.O. Fraction |
|---|---|---|
| 1 | IPA, 85%; water, 15% | 0 |
| 2 | IPA, 76.5%; water, 13.5% | 10 |
| 3 | IPA, 68%; water, 12% | 20 |
| 4 | IPA, 59.5%; water, 10.5% | 30 |
| 5 | K-oleate, 2.5%; water, 97.5% | 0 |
| 6 | K-oleate, 2.5%; water, 87.5% | 10 |
| 7 | K-oleate, 2.5%; water, 82.5% | 15 |
| 8 | K-oleate, 2.5%; water, 77.5% | 20 |
| 9 | K-oleate, 2.5%; water, 72.5% | 25 |
| 10 | Untreated check | |
| 11 | 100% 6E horticultural oil | 0 |
| 12 | 90% 6E horticultural oil | 10 |
| 13 | 80% 6E horticultural oil | 20 |

Both contact/residual and residual activity were measured. Two tests were conducted. Test 2 was simply a repeat of Test 1. In the contact/residual experiment, leaf discs were dipped in the various formulations of Table 1 and placed on paper toweling to drain off excess solution. The leaf discs (four/treatment) were then placed in small petri dishes, having a 6 centimeter diameter, on moistened filter paper.

In the contact/residual experiment, five larvae were placed directly on each of the treated leaf discs immediately after treatment. For measuring residual effects, the larvae (again, 5/leaf disc) were placed on untreated discs adjacent to treated discs in each petri dish. It was assumed that the larvae would eat the untreated discs beore attacking the treated discs.

The results were measured by recording the number of larvae dead and alive on or off the leaf discs. The results are shown in Tables 2-8 below. Also, the feeding damage was recorded by estimating the percentage of leaf disc consumed by the larvae.

TABLE 2

CONTACT/LOOPERS TEST 1
24 HOURS AFTER TREATMENT

| Formulation # | # Live | % Live Off Disc | % Feeding Damage |
|---|---|---|---|
| 1 | 4.75 | 38 | 12.5 |
| 2 | 3.25 | 90 | 2.5 |
| 3 | 3.25 | 67 | 1.25 |
| 4 | 4 | 95 | 1.25 |
| 5 | 5 | 25 | 80 |
| 6 | 4.5 | 68 | 22.5 |
| 7 | 3 | 79 | 7.5 |
| 8 | 3.5 | 88 | 1.25 |
| 9 | 3 | 100 | 0 |
| 10 | 4.75 | 25 | 63.75 |
| 11 | 1.5 | 78 | 0 |
| 12 | 0 | | 0 |
| 13 | .25 | 100 | 0 |

| | # Dead | % Dead on Disc | Total (live + dead) off Disc |
|---|---|---|---|
| 1 | .25 | 0 | 2 |
| 2 | 1.75 | 8 | 4.25 |
| 3 | 1.25 | 0 | 3.5 |
| 4 | 1 | 83 | 4 |
| 5 | 0 | | 1.25 |
| 6 | .25 | 0 | 3.5 |
| 7 | 1.5 | 25 | 3.25 |
| 8 | 1 | 83 | 3.25 |
| 9 | 2 | 83 | 3.5 |
| 10 | .25 | 0 | 1.5 |
| 11 | 3.5 | 56 | 2.25 |
| 12 | 5 | 80 | 1 |
| 13 | 4.75 | 100 | .25 |

TABLE 3

CONTACT/LOOPERS TEST 1
48 HOURS AFTER TREATMENT

| Formulation # | # Live | % Live Off Disc | % Feeding Damage |
|---|---|---|---|
| 1 | 4 | 21 | 68.75 |
| 2 | 1.75 | 100 | 5 |
| 3 | 3 | 77 | 26.25 |
| 4 | 1 | 50 | 1.25 |
| 5 | 4.5 | 100 | 100 |
| 6 | 4.75 | 59 | 50 |
| 7 | 2.5 | 100 | 12.5 |
| 8 | 1.25 | 100 | 2.5 |
| 9 | 1.75 | 72 | 5 |
| 10 | 4 | 13 | 95 |
| 11 | .5 | 100 | 0 |
| 12 | 0 | | 0 |
| 13 | .25 | 100 | 0 |

| | # Dead | % Dead on Disc | Total (live + dead) off Disc |
|---|---|---|---|
| 1 | .75 | 50 | 1.5 |
| 2 | 1.75 | 46 | 2.75 |
| 3 | .25 | 0 | 2.5 |
| 4 | 3.5 | 42 | 2.75 |
| 5 | .25 | 39 | 4.75 |
| 6 | 0 | 0 | 2.75 |
| 7 | 1 | 67 | 3 |
| 8 | 2.75 | 22 | 3.25 |
| 9 | 2.5 | 56 | 2.5 |
| 10 | .5 | 50 | .25 |
| 11 | 4.5 | 54 | 2.5 |
| 12 | 4.5 | 73 | 1.25 |
| 13 | 4.5 | 100 | .25 |

TABLE 4

CONTACT/LOOPERS TEST 1
72 HOURS AFTER TREATMENT

| Formulation # | # Live | % Live Off Disc | % Feeding Damage |
|---|---|---|---|
| 1 | 4 | 25 | 77.5 |
| 2 | .75 | 100 | 15 |
| 3 | 1.5 | 100 | 18.75 |
| 4 | .25 | 100 | 1.25 |
| 5 | 3.25 | 25 | 100 |
| 6 | 3 | 100 | 66.25 |
| 7 | 1.25 | 100 | 25 |
| 8 | .5 | 50 | 5 |
| 9 | 0 | | 7.5 |
| 10 | 3.25 | 0 | 100 |
| 11 | 0 | | 0 |
| 12 | 0 | | 0 |

TABLE 4-continued

CONTACT/LOOPERS TEST 1
72 HOURS AFTER TREATMENT

| 13 | 0 | | 0 |
|---|---|---|---|

| | # Dead | % Dead on Disc | Total (live + dead) off Disc |
|---|---|---|---|
| 1 | 0 | | 1.25 |
| 2 | 1.75 | 0 | 2.5 |
| 3 | 1.25 | 0 | 2.75 |
| 4 | 4.25 | 42 | 2.75 |
| 5 | .75 | | .75 |
| 6 | .75 | 0 | 3.75 |
| 7 | 1.5 | 22 | 2.25 |
| 8 | 3.25 | 45 | 2 |
| 9 | 4 | 35 | 2.75 |
| 10 | 0 | | 0 |
| 11 | 5 | 50 | 2.5 |
| 12 | 5 | 75 | 1.25 |
| 13 | 5 | 85 | .75 |

TABLE 5

CONTACT/LOOPERS TEST 2

| | % Feeding Injury | | |
|---|---|---|---|
| Formulation # | After 24 Hours | After 48 Hours | After 72 Hours |
| 1 | 0 | 0 | 25 |
| 2 | 0 | 3.75 | 7.5 |
| 3 | 0 | 0 | 1.25 |
| 4 | 0 | 0 | 0 |
| 5 | 45 | 75 | 100 |
| 6 | 3.75 | 45 | 37.5 |
| 7 | 0 | 5 | 15 |
| 8 | 1.25 | 1.25 | 5 |
| 9 | 0 | 0 | 0 |
| 10 | 81.25 | 96.25 | 100 |
| 11 | 0 | 0 | 0 |
| 12 | 0 | 0 | 0 |
| 13 | 0 | 0 | 0 |

TABLE 6

RESIDUE/LOOPERS TEST 1

| Formulation # | # Live After 24 Hours | # Live After 48 Hours | # Live After 72 Hours |
|---|---|---|---|
| 1 | 4.5 | 4 | 3 |
| 2 | 4.5 | 4.25 | 3.75 |
| 3 | 5 | 4.75 | 3.25 |
| 4 | 4.75 | 3.25 | 3.5 |
| 5 | 4.75 | 4 | 3 |
| 6 | 5 | 4.5 | 4.25 |
| 7 | 4.5 | 4 | 3.25 |
| 8 | 4.75 | 4.5 | 3.75 |
| 9 | 4.75 | 4 | 2.75 |
| 10 | 5 | 5 | 2.25 |
| 11 | 5 | 2.75 | 1.25 |
| 12 | 3.75 | 2.25 | 1 |
| 13 | 4.75 | 2 | 1 |

TREATED LEAF DISCS:

| | % Feeding Damage | | |
|---|---|---|---|
| Formulation | After 24 Hours | After 48 Hours | After 72 Hours |
| 1 | 22.5 | 87.5 | 100 |
| 2 | 2.5 | 77.5 | 97.5 |
| 3 | 3.75 | 37.5 | 66.25 |
| 4 | 1.25 | 31.25 | 55 |
| 5 | 27.5 | 97.5 | 100 |
| 6 | 1.25 | 77.5 | 97.5 |
| 7 | 0 | 48.75 | 70 |
| 8 | 3.75 | 26.25 | 40 |
| 9 | 0 | 11.25 | 21.25 |
| 10 | 38.75 | 100 | 100 |
| 11 | 3.75 | 16.25 | 16.25 |
| 12 | 1.25 | 3.75 | 7.5 |

TABLE 6-continued

RESIDUE/LOOPERS TEST 1

| 13 | 5 | 5 | 5 |
|---|---|---|---|

UNTREATED LEAF DISCS:

| | % Feeding Damage After |
|---|---|
| Formulation | 24 Hours |
| 1 | 55 |
| 2 | 72.5 |
| 3 | 82.5 |
| 4 | 73.75 |
| 5 | 57.5 |
| 6 | 90 |
| 7 | 88.75 |
| 8 | 81.25 |
| 9 | 86.25 |
| 10 | 72.5 |
| 11 | 90 |
| 12 | 67.5 |
| 13 | 83.75 |

TABLE 7

RESIDUE/LOOPERS TEST 2
TREATED LEAF DISCS:

| | % Feeding Damage | | |
|---|---|---|---|
| Formulation # | After 24 Hours | After 48 Hours | After 72 Hours |
| 1 | 58.75 | 93.75 | 100 |
| 2 | 2.5 | 26.25 | 37.75 |
| 3 | 3.75 | 23.75 | 50 |
| 4 | 1.25 | 11.25 | 21.25 |
| 5 | 85 | 98.75 | 100 |
| 6 | 16.25 | 25 | 31.25 |
| 7 | 6.25 | 16.25 | 37.5 |
| 8 | 7.5 | 8.75 | 5 |
| 9 | 6.25 | 11.25 | 8.75 |
| 10 | 85 | 82.5 | 82.5 |
| 11 | 2.5 | 5 | 3.75 |
| 12 | 3.75 | 1.25 | 0 |
| 13 | 1.25 | 1.25 | 1.25 |

TABLE 8

RESIDUE/LOOPERS

| Formulation # | Drying Time (Min) | # Live | # Dead | % Feeding Injury |
|---|---|---|---|---|
| 1 | 0 | 0 | 5 | 0 |
| 4 | 0 | 0 | 5 | 0 |
| 5 | 0 | 1.75 | 2 | 60 |
| 9 | 0 | 1.25 | 3.75 | 8.75 |
| 11 | 0 | 1 | 4 | 5 |
| 13 | 0 | 0 | 5 | 0 |
| 1 | 5 | .5 | 4.5 | 2.5 |
| 4 | 5 | 2.5 | 2.5 | 3.75 |
| 5 | 5 | 2 | 2.5 | 30 |
| 9 | 5 | .25 | 4.75 | 2.5 |
| 11 | 5 | 0 | 4.75 | 0 |
| 13 | 5 | .25 | 4.75 | 0 |
| 1 | 2 | 2.5 | 2.25 | 38.75 |
| 4 | 2 | 2 | 2 | 5 |
| 5 | 2 | 4 | .75 | 66.25 |
| 9 | 2 | 2 | 2.5 | 6.25 |
| 11 | 2 | 1.75 | 3.25 | 3.75 |
| 13 | 2 | .5 | 4.5 | 1.25 |
| 10 | 0 | 4 | .75 | 81.25 |

Table 2 shows the results for the contat test of Test 1 after 24 hours. Table 3 shows the results for the same contact test for Test 1 after 48 hours. Table 4 shows the results for the contact test for Test 1 after 72 hours. Table 5 shows the results of a contact test for Test 2 which was conducted similarly to Test 1. Table 6 shows the results for the residue test for Test 1. Table 7 shows the results of the residue test for Test 2. Table 8 shows the results of the residue test for leaf drying time.

The contact looper experiments demonstrate that the formulations are effective in killing loopers and reducing feeding injury. Percent feeding damage was evaluated over a 3-day period after the day of treatment; damage did not increase with time. In most cases, all the loopers, both on and off the discs, were dead by the fourth day as shown in Tables 2-4. In Test 2 as shown in Table 5, the data show that feeding injury had increased by the third day. However, all treatments were statistically better than the controls.

In the residual tests, mortality was considerably lower and feeding injury greater than on the contact treated loopers. However, feeding injury (measure of antifeedant property) was again rate related. Table 6 shows the percentage damage over a 4-day period. The Formulations having a higher % T.O. fraction fared better on the third day, with the Formulations having T.O. and K-oleate being the best. Table 8 shows the leaf drying time before the insects were placed on the leaf discs. These data also show the effectiveness of all treatments after one day's observation.

EXAMPLE 2

One contact efficacy test and two residue tests were made using aphids as the target pests and chrysanthemum as the host plant. All tests were made by cutting 2.5 centimeter leaf discs from the treated plant material or by cutting leaf discs from untreated plant material and then dipping the leaf discs into the indicated formulations of Table 1 above. After treatment, the discs were maintained on moist filter paper in small petri dishes.

In the contrast test, five aphids were placed on untreated leaf discs and then the discs were dipped directly into the formulations. In the short term residual experiment, Test 1, the leaf discs were dipped and allowed to drain and "dry," and then five aphids were placed on each leaf disc. The other residue test, Test 2, involved dipping leaves still intact on plants into the Formulations. At 2, 5, and 7 days post-treatment, the leaf discs were removed from the treated plant material and placed in petri dishes. Five aphids were then placed on each leaf disc. Mortality, reproduction, and repellency were recorded 24 and 48 hours after aphids were placed on the leaf discs. The results are shown in Tables 9-12 below. In Tables 9-12, * means that the aphids were placed on the discs at this time, NS means that no sample was taken because of the lack of healthy plant tissue, and PT means post-treatment.

TABLE 9

| RESIDUE/APHIDS TEST 1 | | | | |
|---|---|---|---|---|
| Formulation # | 24 hrs PT # live | 24 hrs PT # missing | 24 hrs PT # nymphs | 24 hrs PT # off |
| 1 | 3.8 | .8 | 0 | 1.8 |
| 2 | 3.4 | 1 | 0 | 2.8 |
| 3 | 2.6 | .8 | 0 | 2.6 |
| 4 | .6 | 1.2 | 0 | 1 |
| 5 | 2 | .6 | 0 | 1.2 |
| 6 | 1.2 | 1.2 | 0 | 1.4 |
| 7 | .6 | 1.4 | 0 | .6 |
| 8 | .2 | 1 | 0 | .2 |
| 9 | .2 | .6 | 0 | .2 |
| 10 | 4.6 | .2 | .8 | .2 |
| Formulation # | 48 hrs PT # live | 48 hrs PT # missing | 48 hrs PT # nymphs | 48 hrs PT # off |
| 1 | 2.2 | 1.6 | .8 | .6 |
| 2 | 1.4 | 1.4 | 0 | 2.4 |
| 3 | .4 | 1.2 | 0 | 1.2 |

TABLE 9-continued

| RESIDUE/APHIDS TEST 1 | | | | |
|---|---|---|---|---|
| 4 | .8 | 1.4 | 0 | .8 |
| 5 | 3 | .6 | .8 | 2.2 |
| 6 | 1.8 | 1 | 0 | 2.4 |
| 7 | .2 | 1.4 | 0 | .4 |
| 8 | .2 | 1 | 0 | .2 |
| 9 | .2 | .6 | 0 | .4 |
| 10 | 4.4 | 4 | 2.8 | .2 |

TABLE 10

| RESIDUE/APHIDS TEST 2 | | | |
|---|---|---|---|
| | Samples Taken | | |
| Formulation # | 2 Days PT # Live 24 Hrs PT | 5 Days PT # Live 24 Hours PT | 7 Days PT* # Live 24 Hours PT |
| 1 | NS** | 4.2 | NS |
| 2 | NS | 4.8 | NS |
| 3 | NS | 3.4 | NS |
| 4 | NS | 3 | NS |
| 5 | 3.6 | 4.4 | 4.4 |
| 6 | 1.2 | .8 | 4.4 |
| 7 | 1 | 1.6 | 2.4 |
| 8 | .4 | 1.4 | 3 |
| 9 | 0 | 1.4 | 1.2 |
| 10 | 4.4 | 5 | 4.8 |
| | 48 Hrs PT | 48 Hrs PT | 48 Hrs PT |
| 1 | NS | 2.2 | NS |
| 2 | NS | 4.4 | NS |
| 3 | NS | 1 | NS |
| 4 | NS | .8 | NS |
| 5 | NS | 2.4 | 3.6 |
| 6 | NS | 1.4 | 3.2 |
| 7 | NS | .2 | 2.6 |
| 8 | NS | 1 | 1 |
| 9 | NS | .4 | .6 |
| 10 | NS | 4.4 | 5 |

TABLE 11

| RESIDUE/APHIDS TEST 2 | | | |
|---|---|---|---|
| | Samples Taken | | |
| Formulation # | 2 Days PT # nymphs 24 Hrs PT | 5 Days PT # nymphs 24 Hours PT | 7 Days PT* # nymphs 24 Hours PT |
| 1 | NS** | .2 | NS |
| 2 | NS | 2.6 | NS |
| 3 | NS | .6 | NS |
| 4 | NS | .4 | NS |
| 5 | .6 | 1.8 | 2 |
| 6 | 0 | 0 | 1.8 |
| 7 | 0 | 0 | .4 |
| 8 | 0 | 0 | 0 |
| 9 | 0 | 0 | 0 |
| 10 | 2.2 | 1.6 | 2.4 |
| | 48 Hrs PT | 48 Hrs PT | 48 Hrs PT |
| 1 | NS | .2 | NS |
| 2 | NS | 2.4 | NS |
| 3 | NS | .4 | NS |
| 4 | NS | 0 | NS |
| 5 | NS | 2 | 1.6 |
| 6 | NS | 0 | 1.8 |
| 7 | NS | 0 | 0 |
| 8 | NS | 0 | .4 |
| 9 | NS | 0 | 0 |
| 10 | NS | 4.8 | 5.4 |

TABLE 12

| RESIDUE/APHIDS TEST 2 | | |
|---|---|---|
| Samples Taken | | |
| 2 Days PT # missing | 5 Days PT # missing | 7 Days PT* # missing |

TABLE 12-continued

| RESIDUE/APHIDS TEST 2 | | | |
|---|---|---|---|
| Formulation # | 24 Hrs PT | 24 Hours PT | 24 Hours PT |
| 1 | NS** | .8 | NS |
| 2 | NS | 0 | NS |
| 3 | NS | 1.2 | NS |
| 4 | NS | .8 | NS |
| 5 | 1 | .6 | .6 |
| 6 | 1.2 | 2.6 | .4 |
| 7 | .4 | 3.2 | 2.4 |
| 8 | .6 | 1.8 | 1.8 |
| 9 | 0 | 2.4 | 2 |
| 10 | .6 | 0 | .2 |
| | 48 Hrs PT | 48 Hrs PT | 48 Hrs PT |
| 1 | NS | 2.2 | NS |
| 2 | NS | .2 | NS |
| 3 | NS | 2.6 | NS |
| 4 | NS | 2 | NS |
| 5 | NS | 2.4 | 1.2 |
| 6 | NS | 2.4 | 1.8 |
| 7 | NS | 4 | 2.4 |
| 8 | NS | 2.6 | 2.2 |
| 9 | NS | 3.4 | 1.8 |
| 10 | NS | .6 | 0 |

All Formulations were phytotoxic to chrysanthemum, especially Formulations 1-4, and thus, testing capabilities were limited. When the leaf discs were dipped and allowed to drain and dry for several minutes before the aphids were placed on them in Test 1, only control Formulations 1 and 5 allowed any survival with much of this occurring off the leaf discs. When the aphids were placed on the leaf discs taken from treated plants 2, 4, and 7 days post-treatment in Test 2, considerable survival occurred but little or no reproduction occurred on any of the treatments except those with the lowest amount of the active ingredient. All aphids were killed when treated directly with the Formulations.

EXAMPLE 3

Several experiments were conducted to evaluate the efficacy of the Formulations on *Tetranychus urticae* using bean as the host plant. The first test involved placing five adults female mites on leaf discs, allowing them to lay eggs for 24 hours, and then dipping the entire disc including the adult mites into the Formulations. All Formulations except the water checks caused 100% mortality within a very short time.

The discs were maintained on moist irrigation matting for five additional days to check the effect of the Formulations on egg hatch. The results indicated that the addition of tall oil neutrals at all the rates tested caused 100% egg mortality as shown in Table 13 below. Some egg hatch did occur in all the "carrier" checks although the number of nymphs in the potassium oleate Formulations 5 was very low and was not significantly different from those with no egg hatch.

TABLE 13

| RESIDUE/MITES TEST 1 5 DAY POST TREATMENT | |
|---|---|
| Formulation # | # nymphs per disc |
| 1 | 13 |
| 2 | 0 |
| 3 | 0 |
| 4 | 0 |
| 5 | 2.33 |
| 6 | 0 |
| 7 | 0 |
| 8 | 0 |
| 9 | 0 |

TABLE 13-continued

| RESIDUE/MITES TEST 1 5 DAY POST TREATMENT | |
|---|---|
| Formulation # | # nymphs per disc |
| 10 | 16.33 |

Severe phytotoxicity to bean prevented normal residual testing in which the leaf discs are dipped or plants treated and then leaf disc taken, or mites confined on them at regular post-treatment intervals. However, a residual test was conducted using microliter applicators to apply the Formulations to leaf discs. The Formulations were applied and five female adults were confined to each disc 24 hours later. The results are summarized in Table 14 below.

A total of ten microliters of each Formulation included in this test was applied to the lower surface of leaf discs. Each Formulation used was applied in two different droplet sizes, 0.001 mls and 0.002 mls.

TABLE 14

| MICROLITER/MITES TEST 1 | | | |
|---|---|---|---|
| 5 DAYS POST-TREATMENT | | | |
| No. and size of drops | Formulation # | # Dead Per Disc | # Eggs Per Disc |
| 10-.001 mls | 1 | .5 | 91.75 |
| 5-.002 mls | | 0 | 111.75 |
| 10-.001 mls | 2 | 1.25 | 91.75 |
| 5-.002 mls | | .75 | 87.75 |
| 10-.001 mls | 6 | .5 | 81.5 |
| 5-.002 mls | | 1 | 72 |
| 10-.001 mls | 5 | 0 | 93.25 |
| 5-.002 mls | | .5 | 67 |
| 10-.001 mls | H₂O check | .25 | 91.75 |
| 7 DAYS POST-TREATMENT | | | |
| No. and size of drops | Formulation # | # Dead Per Disc | # Missing Per Disc | # nymphs Per Disc |
| 10-.001 mls | 1 | .5 | 1 | 21.75 |
| 5-.002 mls | | .5 | .5 | 28.5 |
| 10-.001 mls | 2 | 1.5 | 1.25 | 18.75 |
| 5-.002 mls | | .75 | 1.75 | 18 |
| 10-.001 mls | 6 | .5 | 1.5 | 12.25 |
| 5-.002 mls | | 1.25 | 1 | 11 |
| 10-.001 mls | 5 | 0 | .5 | 13 |
| 5-.002 mls | | .75 | 1.25 | 11.5 |
| 10-.001 mls | H₂O check | .5 | .5 | 17.25 |

The Formulations tested in this manner caused very little mortality to adults and did not appear to deter feeding on the leaf discs although mites did not appear to feed in the area that droplets were applied. After one week, the number of nymphs present on each disc was probably not significantly different when the number of live adults present were taken into account. This test indicates that the entire leaf surface should be sprayed to ensure efficacy.

Having described the invention in detail and by reference to preferred embodiments thereof, it will be apparent that modifications and variations are possible without departing from the scope of the invention defined in the appended claims.

What is claimed is:

1. A method for protecting plants from insects, mites, and similar pests which comprises the step of applying tall oil neutrals to plants in an amount effective to protect said plants from said insects, mites, and similar pests.

2. The method of claim 1 wherein said tall oil neutrals are applied to said plants as a solution or an oil-in-water dispersion.

3. The method of claim 2 wherein said tall oil neutrals are present in said solution or dispersion in an amount of about 5 to 30% by weight.

4. The method of claim 3 wherein said solution or dispersion includes isopropyl alcohol.

5. The method of claim 3 wherein said dispersion includes potassium oleate.

6. The method of claim 1 wherein said tall oil neutrals are applied to said plants as a solution formed by the addition of said tall oil neutrals to a horticultural oil.

7. The method of claim 2 wherein said solution or dispersion is applied to said plants by spraying said solution or dispersion on said plants.

8. The method of claim 7 wherein said solution or dispersion is applied to the leaves of said plant.

* * * * *